(12) United States Patent
Karicherla et al.

(10) Patent No.: US 7,347,826 B1
(45) Date of Patent: Mar. 25, 2008

(54) PACKAGING SENSORS FOR LONG TERM IMPLANT

(75) Inventors: Annapurna Karicherla, Valencia, CA (US); John W. Poore, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 275 days.

(21) Appl. No.: 10/688,687

(22) Filed: Oct. 16, 2003

(51) Int. Cl.
*A61B 5/00* (2006.01)
*A61B 5/04* (2006.01)
*A61B 5/02* (2006.01)

(52) U.S. Cl. ............ 600/549; 600/372; 600/373; 600/374; 600/375; 600/377; 600/378; 600/379; 600/380; 600/381; 600/393; 600/394; 600/485; 600/486; 600/488; 600/505

(58) Field of Classification Search .......... 600/372, 600/373, 374, 375, 377, 378, 379, 380, 381, 600/393, 394, 485, 486, 488, 505, 549; 174/52.3
See application file for complete search history.

(56) References Cited

U.S. PATENT DOCUMENTS

| 5,013,396 A | | 5/1991 | Wise et al. ............ 156/628 |
| 5,113,868 A | * | 5/1992 | Wise et al. ............ 600/488 |
| 5,674,258 A | | 10/1997 | Henschel et al. ......... 607/19 |
| 5,750,926 A | * | 5/1998 | Schulman et al. ........ 174/52.3 |
| 5,843,135 A | | 12/1998 | Weijand et al. .......... 607/17 |
| 5,911,738 A | | 6/1999 | Sikorski et al. .......... 607/19 |
| 6,038,475 A | | 3/2000 | Sikorski et al. .......... 607/19 |
| 6,223,081 B1 | | 4/2001 | Kerver ................... 607/17 |
| 6,844,023 B2 | | 1/2005 | Schulman et al. ........ 427/2.24 |
| 2003/0078484 A1 | | 4/2003 | Schulman et al. ........ 600/373 |

FOREIGN PATENT DOCUMENTS

| EP | 0798016 A2 | 10/1997 |
| EP | 0798016 A3 | 12/1998 |
| WO | WO 90/06723 | 6/1990 |
| WO | WO 99/20340 | 4/1999 |

* cited by examiner

*Primary Examiner*—Max F. Hindenburg
*Assistant Examiner*—Jeffrey G Hoekstra

(57) ABSTRACT

According to this technique of packaging a sensor device implantable in a living body so as to provide protection of the sensor device and to the living body itself, an electrical conductor of the sensor device is sealed in an insulating substrate extending between proximal and distal ends. The distal end of the electrical conductor is externally connected to an external sensor on the sensor device and the proximal end of the electrical conductor is externally connected to a distal end of a lead wire extending proximally to a pulse generator and these connections are embedded in an insulative sheath. The external sensor, substrate, and insulative sheath are encapsulated in a thin film of hermetic material without interference with the lead wire. In another embodiment, a layer of insulating material may underlie the hermetic material to encapsulate the external sensor and the substrate.

31 Claims, 3 Drawing Sheets

PACKAGING SENSORS FOR LONG TERM IMPLANT

FIELD OF THE INVENTION

The present invention relates generally to implantable medical devices, and more particularly, to robust packaging for both mechanically and chemically providing adequate protection of the medical device itself and protection to the body in which it is implanted.

BACKGROUND OF THE INVENTION

Smart packaging is an important consideration in the manufacture of an implantable device. The device housing has to be robust both mechanically and chemically to provide adequate protection from the harsh environment of the human body and, at the same time must provide protection to the body in which it is implanted.

In one instance, as disclosed in U.S. Pat. No. 5,013,396 to Wise et al., an ultraminiature capacitive pressure sensor having a silicon diaphragm and rim structure is made with a simple double-diffusion process. This novel diaphragm and rim structure is part of a silicon transducer chip which is electrostatically bonded to a glass support plate prior to removal of all of the wafer except for the diaphragm and rim structure. The novel diaphragm and rim structure features a very small rim area, thus allowing the transducer to be constructed in ultraminiature form. Thus, a capacitive pressure sensor can be mounted, for example, in a 0.5 millimeter OD multisite cardiac catheter suitable for measuring blood pressure gradients inside the coronary artery of the heart. The silicon pressure transducer preferably includes supporting interface circuitry on a chip fastened to the same glass support plate as the diaphragm and rim structure. However, no concern is expressed in the disclosure for protecting the pressure sensor in the body.

U.S. Pat. No. 5,674,258 to Henschel et al. discloses a packaged integrated accelerometer. In this instance, a method is provided for surface mounting a piezoceramic accelerometer directly to a hybrid circuit within a hermetically sealed pacemaker housing.

U.S. Pat. No. 5,843,135 to Weijand et al. discloses a pacing lead incorporating both a sensor, e.g., a pressure sensor, and an electrode for pacing and sensing, the lead being connected to a pacemaker which delivers pacing pulses to the electrode, the pacemaker also receiving and processing cardiac signals from the electrode and sensor information from the sensor. Again, however, there is no mention of packaging for protection of the sensor or of the body.

U.S. Pat. Nos. 5,911,738 and 6,038,475, both to Sikorski et al., provide a method of and apparatus for coupling an accelerometer within a cardiac pacemaker, and by providing a structure which improves substantially the shock survivability of same. In this instance, an accelerometer assembly comprises at least three electrodes electrically isolated from one another in a piezoelectric sub-assembly. The sub-assembly is covered at least partially with an external electrically conductive layer that has been laser scribed or cut to provide electrical isolation of each of the electrodes from the other electrodes. At least one of the electrodes is an internal electrode disposed between opposing sheets of piezoelectric material, and forms an internal electrically conductive layer to which electrical connection is possible from the external surface of the sub-assembly. The remaining two electrodes are external electrodes and may be connected electrically in parallel across the internal electrode to provide a high output signal.

In U.S. Pat. No. 6,223,081 to Kerver, a pacemaker contains a pressure sensor in combination with a pacing lead which connects stimulus pulses to the patient's heart and which is operatively connected to the pacemaker so as to transmit cardiac pressure signals to the pressure sensor. However, once again, there is no mention of or concern for protective packaging of the pressure sensor.

It was with knowledge of the foregoing state of the technology that the present invention has been conceived and is now reduced to practice.

SUMMARY

According to this technique of packaging a sensor device implantable in a living body so as to provide protection of the sensor device and to the living body itself, an electrical conductor of the sensor device is sealed in an insulating substrate extending between proximal and distal ends. The distal end of the electrical conductor is externally connected to an external sensor on the sensor device and the proximal end of the electrical conductor is externally connected to a distal end of a lead wire that leads to an implantable medical device, and the distal connections are embedded in an insulative deposit of protective material. The external sensor, substrate, and insulative deposit of protective material are encapsulated in a thin film of hermetic material without interference with the lead wire. In another embodiment, a layer of insulating material may underlie the hermetic material to encapsulate the external sensor and some parts of the substrate.

As noted earlier, smart packaging is a very important part of making an implantable device. The device housing has to be sufficiently robust, both mechanically and chemically, to provide adequate protection from the human body. Indeed, packaging the pressure sensor, retaining its integrity and sensitivity, and protecting the device have long been a pursuit for those in the industry. The present invention proposes a robust and hermetic seal packaging technique for an implantable sensor without endangering device integrity and is a three step effort.

The packaging of the pressure sensor is performed with two key objectives in mind: sensor integrity and hermetic sealing of the device. The sensor is packaged in three stages. The first step is to seal the electrical conductors of the sensor in an insulating substance such as ceramic or glass. Then, as a possible second step, a very thin film (on the order of microns in thickness) of insulating material such as parylene is coated over the device as an internal layer. This is proposed, but not absolutely necessary, to prevent any contact between the device components and the external metallic packaging material. With this step, care must be taken to achieve a continuous, pinhole free, film to avoid any damage to the sensor. The substrate would be selectively masked before growing parylene (or other suitable insulating material) on the device. The third step in the process is to layer a thin film of titanium, gold, carbon, or any other suitable hermetic material onto the parylene coated device including part of the substrate. However, the titanium coating (or any other hermetic coating) must be selectively applied onto the substrate to prevent contact between the conductors and the hermetic coating material. The titanium, or other hermetic coating, can be applied in many different ways such as by lamination, electroplating, vapor deposition (physical vapor deposition, chemical vapor deposition), and the like. The selective deposition process will ensure that every region coated with insulating material such as parylene is also coated with the hermetic material such as titanium, preventing absorption of moisture through parylene which could potentially provide a path for it to enter into device housing.

One feature, then, of the present invention is the provision of a unique technique for packaging a lead assembly connecting an implantable medical device for providing stimulating pulses to selected body tissue.

A primary feature of the present invention is the provision of such a technique for packaging a lead assembly incorporating a sensor for sensing pressure or other parameters wherein the lead assembly is intended for long term implant.

Yet another feature of the present invention is the provision of such a technique for packaging a lead assembly including the steps of sealing an electrical conductor of the sensor device extending between proximal and distal ends in a substrate, externally connecting the distal end of the electrical conductor to an external sensor on the sensor device, externally connecting the proximal end of the electrical conductor to a distal end of a lead wire extending proximally to a pulse generator, embedding the connection between the distal end of the electrical conductor and the external sensor in an insulative deposit of protective material, and encapsulating the external sensor, substrate, and insulative deposit of protective material in a thin film of hermetic material without interference with the lead wire.

Still another feature of the present invention is the provision of such a technique for packaging a lead assembly which includes the step of encapsulating the external sensor and the substrate in a layer of insulating material without interference with the lead wire.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
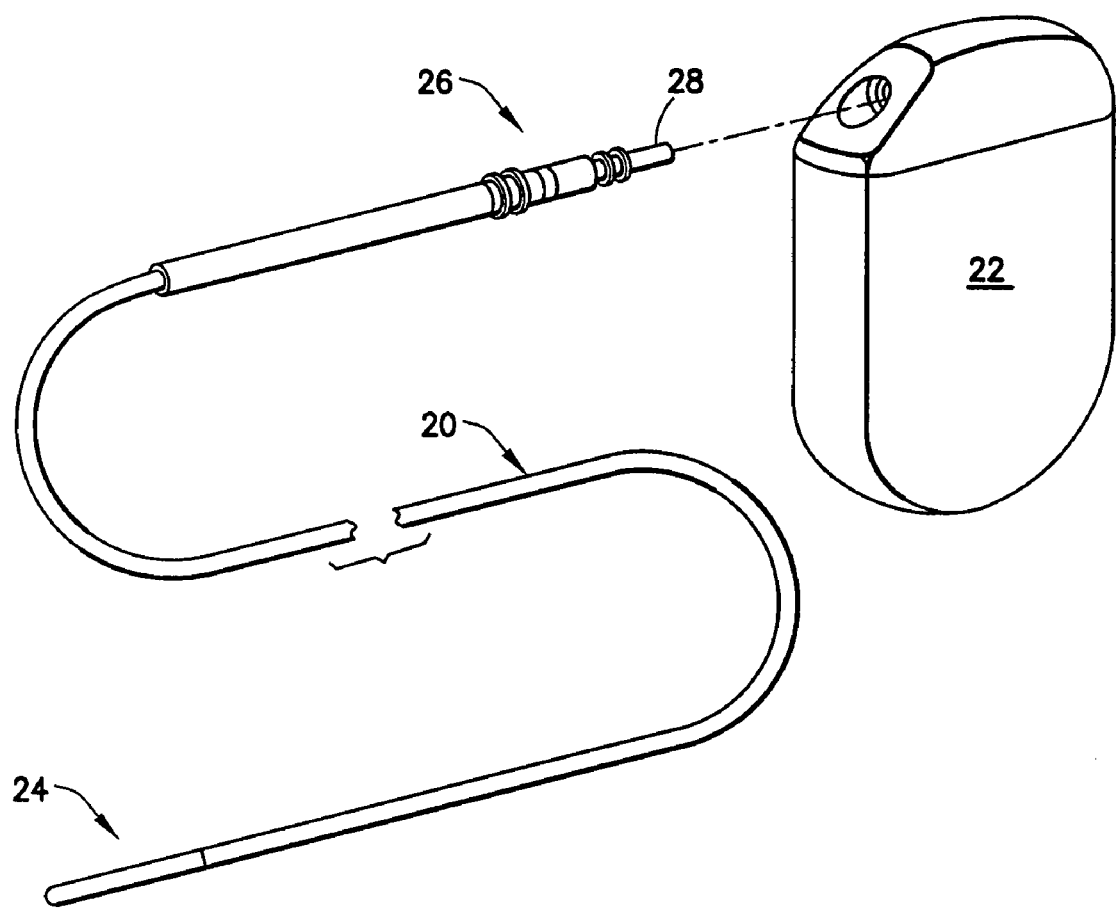
FIG. 1 is a diagrammatic perspective view illustrating an implantable lead system in combination with a pulse generator, the lead system incorporating a packaged sensor embodying the present invention.

Refer now to the drawings and, initially, to FIG. 1 in which is shown an implantable lead 20 used in combination with an implantable stimulation device or pulse generator 22 such as a pacemaker or defibrillator and interconnects a sensor device 24 intended to be introduced into a living body, for example, into an organ such as the heart, and an electrical connector 26 at a proximal end 28 for attachment to the stimulation device. Although the present invention will be described with reference to the embodiments shown in the drawings, it should be understood that the present invention can be embodied in many alternate forms or embodiments. For example, the sensor device 24 may be located inside the lead 20 at various other locations than the one illustrated. Also, a number of sensor devices 24 could be incorporated into the lead 20. In addition, any suitable size, shape or type of elements or materials could be used.

Figure 2:
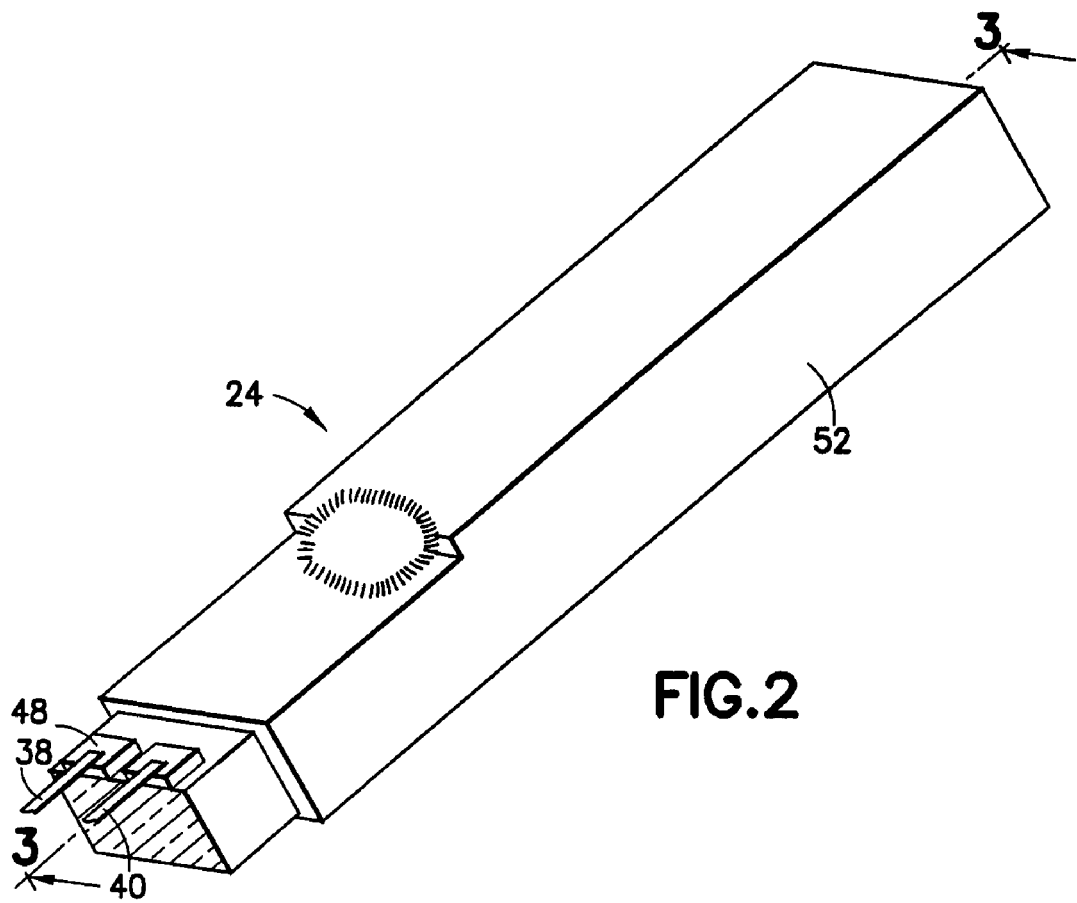
FIG. 2 is a detail perspective view, certain portions being cut away and shown in section, of the packaged sensor illustrated in FIG. 1.
Figure 3:
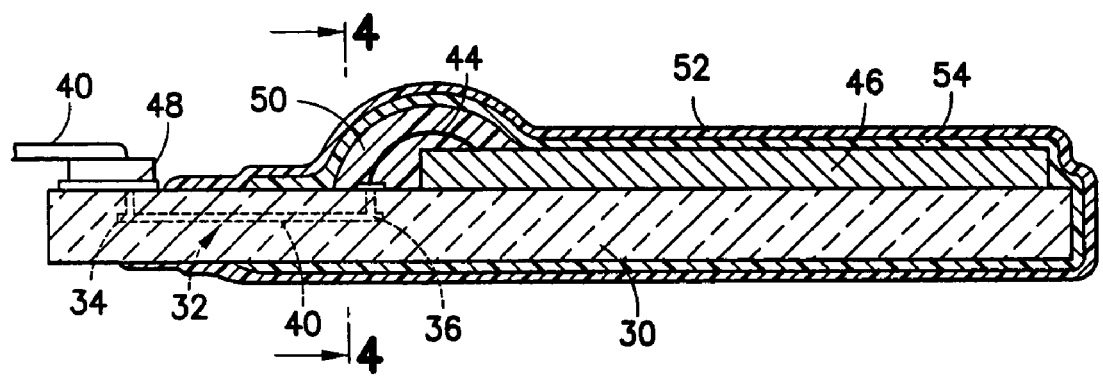
FIG. 3 is a cross section view generally taken along line 3-3 in FIG. 2.
Figure 4:
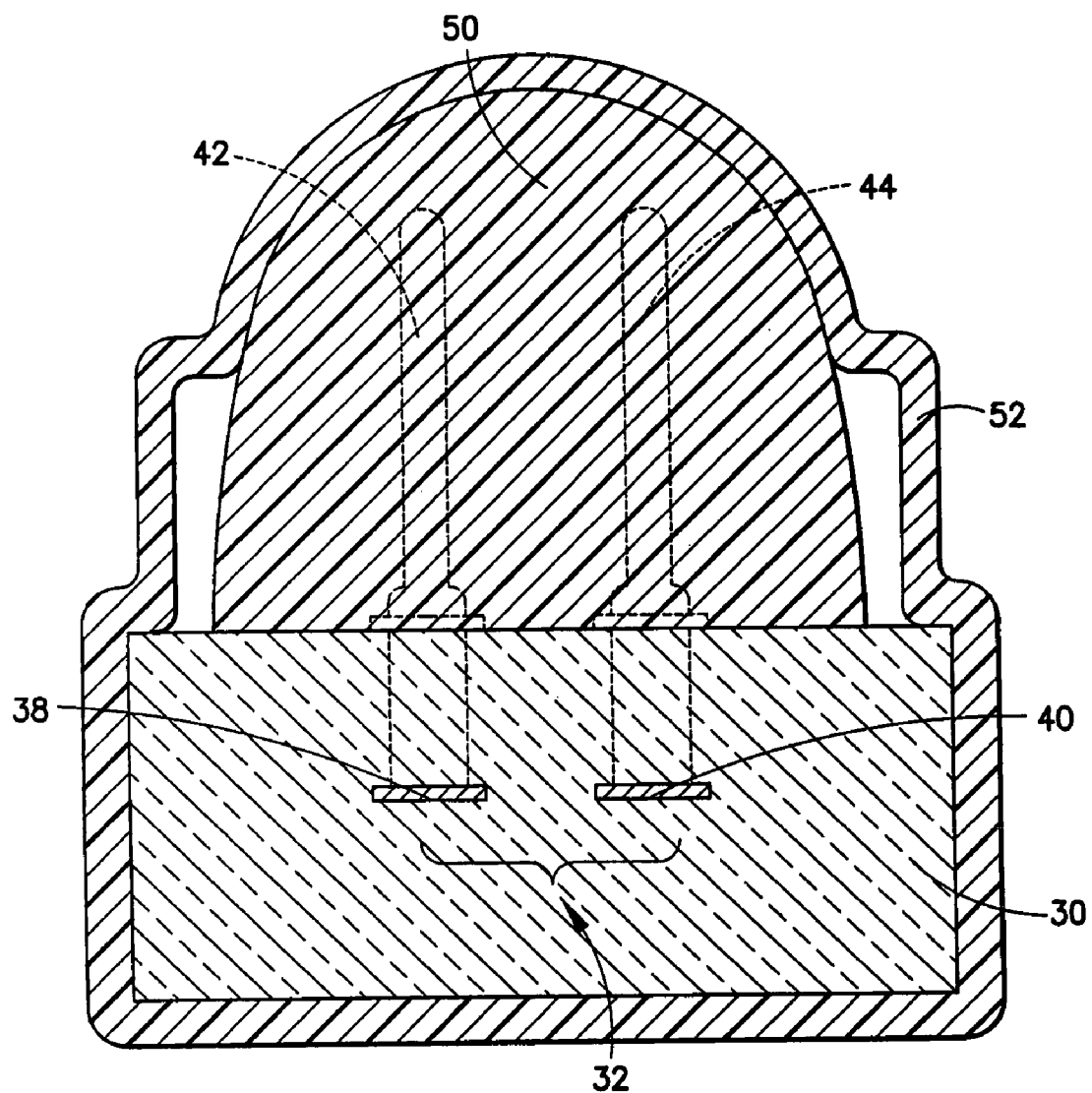
FIG. 4 is a cross section view generally taken along line 4-4 in FIG. 3.

For a more detailed description of the invention, turn now to FIGS. 2, 3, and 4. The sensor device 24 is packaged so as to provide protection of the sensor device itself in the environment of the living body and also to provide protection to the living body from the sensor device. To this end, the packaged sensor device 24 includes an insulating substrate 30 with a feedthrough region 32 extending between proximal and distal ends 34, 36, respectively, of the substrate. The substrate 30 may be composed, for example, of ceramic material or glass. Electrical conductors 38 and 40 extending from the electrical connector 26 are received in the feedthrough region 32 and extend between the proximal and distal ends of the feedthrough region.

Bond wires 42, 44 connect, respectively, the distal ends of the electrical conductors 38, 40 to an external sensor 46 on the substrate 30 and the electrical conductors may be attached to the substrate 30 by means of a conductive pad 48 such as a Kovar pad for introduction to the feedthrough region 32. The sensor 46 may be a temperature sensor or a pressure sensor or it may be, for example, an integrated pressure and temperature sensor chip, a catheter chip manufactured by Fraunhofer Institut für Mikroelektronische Schaltungen und Systeme of Duisburg, Germany being suitable for purposes of the invention. It will be apparent to those skilled in the art that sensor 46 may be any suitable sensor, for example, electrical sensors, transducers, and the like.

An insulative deposit of protective material 50 composed, for example, of epoxy is applied to fully embed the bond wires 42, 44 to electrically insulate them from each other and from all other electrically conductive components which may be in the vicinity of the sensor device 24. Finally, at least the external sensor 46 and the substrate 30, and part of the insulative deposit of protective material 50, are encapsulated in a thin film 52 of hermetic material, for example, gold, titanium, platinum or carbon based materials such as amorphous carbon, diamond like carbon and diamond. However, it is important that the thin film 52, preferably with a thickness in the range of about 10 nm to 0.1 mm, must be applied so as not to interfere with the conductivity of the lead 20.

While not necessary for the performance of the invention, it is desirable to encapsulate at least the external sensor 46 and the substrate 30 in a layer of insulating material 54 which may be composed of parylene or other suitable insulating or non-conductive material. In one embodiment, insulating material 54 has a thickness in the range of about 5.0 nm to 0.5 mm. As with the thin film 52, the insulating material 54 must be applied so as not to interfere with the conductivity of the lead 20.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A pressure sensor device implantable in a living body, the pressure sensor device comprising:
   an insulating substrate that defines a feedthrough region, the insulating substrate having a first outer surface and a second outer surface, the first outer surface of the insulating substrate opposing the second outer surface of the insulating substrate;
   a pressure sensor having a first outer surface and a second outer surface, the first outer surface of the pressure sensor opposing the second outer surface of the pressure sensor, and the pressure sensor directly mounted on the insulating substrate such that the first outer surface of the pressure sensor is in contact with the second outer surface of the insulating substrate;
   an electrical conductor received in the feedthrough region;
   a bond wire connected to the electrical conductor and to the pressure sensor, wherein the bond wire is embedded in an insulative sheath;
   a lead connected to the electrical conductor and configured for connection to an implantable medical device; and
   a thin film of hermetic material encapsulating both the second outer surface of the pressure sensor and the first outer surface of the insulating substrate, an inner surface of the thin film directly contacting the second outer surface of the pressure sensor and the first outer surface of the insulating substrate to form a voidless encapsulation of the pressure sensor and the insulating substrate;
   wherein the thin film of hermetic material is a continuous thin film encapsulating both the second outer surface of the pressure sensor and the first outer surface of the insulating substrate.

2. The implantable sensor device as set forth in claim 1 wherein the insulating substrate is composed of at least one of ceramic and glass.

3. The implantable sensor device as set forth in claim 1 wherein the pressure sensor is an integrated pressure sensor and temperature sensor unit.

4. The implantable sensor device as set forth in claim 1 wherein the hermetic material is at least one of titanium, gold, platinum, and carbon.

5. The implantable sensor device as set forth in claim 1 wherein the thickness of the thin film of hermetic material is in the range of about 10 nm to 0.1 mm.

6. The implantable sensor device as set forth in claim 1 and further comprising:
   a pad of conductive material intermediate, and in electrical continuity with, the lead and with the electrical conductor.

7. The implantable sensor device as set forth in claim 1 wherein the lead is an implantable lead to pace and sense a heart.

8. The implantable sensor device as set forth in claim 1 wherein the thin film of hermetic material in contact with the second outer surface of the pressure sensor is exposed to the living body, and wherein the second outer surface of the pressure sensor and the thin film of hermetic material in contact with the second outer surface of the pressure sensor deflect in response to pressure changes in the living body.

9. The implantable sensor device as set forth in claim 1 wherein the second outer surface of the pressure sensor comprises a diaphragm to measure pressure, wherein the thin film of hermetic material is in contact with the diaphragm, wherein the thin film of hermetic material in contact with the diaphragm is exposed to the living body, and wherein the diaphragm and the thin film of hermetic material in contact with the diaphragm deflect in response to a change in pressure in the living body.

10. The implantable sensor device as set forth in claim 1 wherein the pressure sensor is a capacitive pressure sensor, wherein the second outer surface of the pressure sensor comprises a diaphragm and the thin film of hermetic material is in contact with the diaphragm, wherein the thin film of hermetic material in contact with the diaphragm is exposed to the living body, and wherein the diaphragm and the thin film of hermetic material in contact with the diaphragm are defectively responsive to pressure changes in the living body.

11. An implantable medical device comprising:
    a pulse generator;
    an implantable lead having a distal portion and a proximal portion, the proximal portion connected to the pulse generator; and
    a pressure sensor device connected to the implantable lead, the pressure sensor device comprising:
    an insulating substrate that defines a feedthrough region, the insulating substrate having a first outer surface and a second outer surface, and the first outer surface of the insulating substrate opposing the second outer surface of the insulating substrate;
    a pressure sensor having a first outer surface and a second outer surface, the first outer surface of the pressure sensor opposing the second outer surface of the pressure sensor, and the pressure sensor mounted directly on the insulating substrate such that the first outer surface of the pressure sensor is in contact with the second outer surface of the insulating substrate;
    an electrical conductor received in the feedthrough region, the electrical conductor electrically coupled to the implantable lead;
    a layer of insulating material encapsulating both the pressure sensor and the insulating substrate, an inner surface of the layer of insulating material directly contacting the first outer surface of the insulating substrate and the second outer surface of the pressure sensor to form a voidless encapsulation of the pressure sensor and the insulating substrate; and
    a thin film of hermetic material encapsulating the layer of insulating material, an inner surface of the thin film of hermetic material directly contacting an outer surface of the layer of insulating material to form a voidless encapsulation of the layer of insulating material;
    wherein the thin film of hermetic material is a continuous thin film encapsulating both the second outer surface of the pressure sensor and the first outer surface of the insulating substrate.

12. The implantable medical device as set forth in claim 11 and further comprising:
a bond wire connecting the electrical conductor to the pressure sensor; and
an insulative deposit of protective material embedding the bond wire;
wherein the layer of insulating material encapsulates the insulative deposit of protective material.

13. The implantable medical device as set forth in claim 11
wherein a proximal end of the pressure sensor device is connected to the distal end of the implantable lead.

14. The implantable medical device as set forth in claim 11
wherein the insulating substrate is composed of at least one of ceramic and glass.

15. The implantable medical device as set forth in claim 11
wherein the pressure sensor is an integrated pressure sensor and temperature sensor unit.

16. The implantable medical device as set forth in claim 11
wherein the hermetic material is at least one of titanium, gold, platinum, and carbon.

17. The implantable medical device as set forth in claim 11
wherein the thickness of the thin film of hermetic material is in the range of about 10 nm to 0.1 mm.

18. The implantable medical device as set forth in claim 11
wherein the thickness of the layer of insulating material is in the range of about 5.0 nm to 0.5 mm.

19. The implantable medical device as set forth in claim 11
wherein the implantable medical device is a cardiac pacemaker; and
wherein the implantable lead paces and senses a heart.

20. The implantable medical device as set forth in claim 11
wherein the thin film of hermetic material in contact with the second outer surface of the of the pressure sensor is exposed to a living body, and wherein the second outer surface of the pressure sensor, the layer of insulating material, and the thin film of hermetic material deflect in response to pressure changes in the living body.

21. The implantable medical device as set forth in claim 11
wherein the second outer surface of the pressure sensor comprises a diaphragm to measure pressure in a living body, wherein the layer of insulating material is in contact with the diaphragm, wherein the thin film of hermetic material is exposed to the living body, and wherein the diaphragm, the layer of insulating material, and the thin film of hermetic material deflect in response to a change in pressure in the living body.

22. The implantable medical device as set forth in claim 11
wherein the pressure sensor is a capacitive pressure sensor, wherein the second outer surface of the pressure sensor comprises a diaphragm and the layer of insulating material is in contact with the diaphragm, wherein the thin film of hermetic material in contact with the layer of insulating material is exposed to a living body, and wherein the diaphragm, the layer of insulating material, and the thin film of hermetic material is deflectively responsive to pressure changes in the living body.

23. An implantable medical device comprising:
a pulse generator;
an implantable lead having a distal portion and a proximal portion, the proximal portion connected to the pulse generator; and
a pressure sensor device connected to the implantable lead, the pressure sensor device comprising:
an insulating substrate that defines a feedthrough region, the insulating substrate having a first outer surface and a second outer surface, and the first outer surface of the insulating substrate opposing the second outer surface of the insulating substrate;
a pressure sensor having a first outer surface and a second outer surface, the first outer surface of the pressure sensor opposing the second outer surface of the pressure sensor, and the pressure sensor directly mounted on the insulating substrate such that the first outer substrate of the pressure sensor is in contact with the second outer surface of the insulating substrate;
an electrical conductor received in the feedthrough region, the electrical conductor electrically coupled to the implantable lead; and
a thin film of hermetic material encapsulating both the insulating substrate and the pressure sensor, an inner surface of the thin film of hermetic material directly contacting the first outer surface of the insulating substrate and the second outer surface of the pressure sensor to form a voidless encapsulation of the insulating substrate and the pressure sensor;
wherein the thin film of hermetic material is a continuous thin film encapsulating both the second outer surface of the pressure sensor and the first outer surface of the insulating substrate.

24. The implantable medical device as set forth in claim 23 and further comprising:
a bond wire connecting the electrical conductor to the pressure sensor; and
an insulative deposit of protective material embedding the bond wire;
wherein the thin film of hermetic material encapsulates the insulative deposit of protective material.

25. The implantable medical device as set forth in claim 23
wherein a proximal end of the pressure sensor device is connected to the distal end of the implantable lead.

26. The implantable medical device as set forth in claim 23
wherein the insulating substrate is composed of at least one of ceramic and glass.

27. The implantable medical device as set forth in claim 23
wherein the pressure sensor is an integrated pressure sensor and temperature sensor unit.

28. The implantable medical device as set forth in claim 23
wherein the hermetic material is at least one of titanium, gold, platinum, and carbon.

29. The implantable medical device as set forth in claim 23
wherein the thin film of hermetic material in contact with the second outer surface of the of pressure sensor is exposed to a living body, and wherein the second outer surface of the pressure sensor and the thin film of hermetic material in contact with the second outer surface of the pressure sensor deflect in response to pressure changes in the living body.

30. The implantable medical device as set forth in claim 23 wherein the second outer surface of the pressure sensor comprises a diaphragm to measure pressure in a living body, wherein the thin film of hermetic material is in contact with the diaphragm, wherein the thin film of hermetic material in contact with the diaphragm is exposed to the living body, and wherein the diaphragm and the thin film of hermetic material in contact with the diaphragm deflect in response to a change in pressure in the living body.

31. The implantable medical device as set forth in claim 23 wherein the pressure sensor is a capacitive pressure sensor, wherein the second outer surface of the pressure sensor comprises a diaphragm and the thin film of hermetic material is in contact with the diaphragm, wherein the thin film of hermetic material in contact with the diaphragm is exposed to a living body, and wherein the diaphragm and the thin film of hermetic material is deflectively responsive to pressure changes in the living body.

* * * * *